United States Patent
Ma et al.

(10) Patent No.: US 11,903,829 B1
(45) Date of Patent: Feb. 20, 2024

(54) EXPANDABLE SHEATH FOR TRANSCATHETER DELIVERY SYSTEM AND DELIVERY SYSTEM

(71) Applicant: VENUS MEDTECH (HANGZHOU) INC., Zhejiang (CN)

(72) Inventors: Renzheng Ma, Zhejiang (CN); Jianan Wang, Zhejiang (CN); Meirong Liu, Zhejiang (CN); Yuxuan Du, Zhejiang (CN)

(73) Assignee: VENUS MEDTECH (HANGZHOU) INC., Hangzhou (CN)

( * ) Notice: Subject to any disclaimer, the term of this patent is extended or adjusted under 35 U.S.C. 154(b) by 0 days.

(21) Appl. No.: 18/212,197

(22) Filed: Jun. 21, 2023

Related U.S. Application Data

(63) Continuation of application No. PCT/CN2023/101123, filed on Jun. 19, 2023.

(30) Foreign Application Priority Data

May 9, 2023 (CN) .......................... 202310511682.1

(51) Int. Cl.
   *A61F 2/24* (2006.01)
   *A61M 25/00* (2006.01)

(52) U.S. Cl.
   CPC ....... *A61F 2/2436* (2013.01); *A61M 25/0074* (2013.01)

(58) Field of Classification Search
   None
   See application file for complete search history.

(56) References Cited

U.S. PATENT DOCUMENTS

| | | | | |
|---|---|---|---|---|
| 2004/0087965 | A1* | 5/2004 | Levine | A61F 2/95 623/1.11 |
| 2004/0181237 | A1* | 9/2004 | Forde | A61B 17/12122 623/1.11 |
| 2005/0049577 | A1* | 3/2005 | Snell | A61M 25/04 264/171.16 |
| 2005/0137696 | A1* | 6/2005 | Salahieh | A61F 2/2439 623/2.11 |
| 2010/0331949 | A1* | 12/2010 | Habib | A61B 18/1477 623/1.11 |
| 2011/0301702 | A1* | 12/2011 | Rust | A61F 2/2418 623/2.11 |

(Continued)

*Primary Examiner* — Shaun L David

(57) ABSTRACT

An expandable sheath for transcatheter delivery system is disclosed, including a tube having opposing distal and proximal ends in its axial direction. The distal end is provided with a plurality of support rods arranged at intervals in a circumferential direction of the tube, and the support rods extending axially and having relative converged and flared configurations. More than two connecting strips are provided in the axial direction between two adjacent support rods. The connecting strip extends in a curved path and undulates in the circumferential direction, and undulation degrees of the connecting strips increase sequentially from the proximal end to the distal end. The connecting strip has a first connecting portion and a second connecting portion respectively connected with two adjacent support rods in the circumferential direction, and the first connecting portion and the second connecting portion are located at different axial levels of the tube.

16 Claims, 6 Drawing Sheets

(56) References Cited

U.S. PATENT DOCUMENTS

| | | | |
|---|---|---|---|
| 2012/0239142 A1* | 9/2012 | Liu | A61F 2/2418 |
| | | | 623/2.11 |
| 2014/0107758 A1* | 4/2014 | Glazier | A61F 2/2436 |
| | | | 623/1.12 |
| 2014/0316518 A1* | 10/2014 | Kheradvar | A61F 2/2439 |
| | | | 623/2.11 |
| 2016/0206426 A1* | 7/2016 | Khoynezhad | A61F 2/2433 |
| 2017/0056061 A1* | 3/2017 | Ogle | A61B 17/320725 |
| 2017/0056172 A1* | 3/2017 | Salahieh | A61F 2/2412 |
| 2018/0064462 A1* | 3/2018 | Walzman | A61B 17/320758 |
| 2018/0206862 A1* | 7/2018 | Long | A61B 17/221 |
| 2019/0290818 A1* | 9/2019 | Tuseth | A61M 60/165 |
| 2020/0054432 A1* | 2/2020 | Martin | A61F 2/011 |
| 2020/0352759 A1* | 11/2020 | Sakaya | A61F 2/958 |
| 2021/0298926 A1* | 9/2021 | Shobayashi | A61F 2/76 |
| 2022/0168014 A1* | 6/2022 | Dale | A61F 2/2466 |
| 2022/0401216 A1* | 12/2022 | Bian | A61F 2/962 |
| 2023/0038490 A1* | 2/2023 | Griswold | A61F 2/2436 |
| 2023/0054898 A1* | 2/2023 | Gurovich | A61F 2/966 |
| 2023/0172638 A1* | 6/2023 | Gillespie | A61B 17/22031 |
| | | | 623/1.11 |
| 2023/0200840 A1* | 6/2023 | Kowalski | A61M 25/0147 |
| | | | 606/159 |

* cited by examiner

EXPANDABLE SHEATH FOR TRANSCATHETER DELIVERY SYSTEM AND DELIVERY SYSTEM

CROSS-REFERENCE TO RELATED APPLICATIONS

The present application is a Continuation Application of PCT Application No. PCT/CN2023/101123, filed on Jun. 19, 2023, which claims priority of Chinese Patent Application No. CN202310511682.1, filed on May 9, 2023, the entire contents of which are hereby incorporated by reference.

TECHNICAL FIELD

The present disclosure relates to the technical field of a medical device, in particular to an expandable sheath for transcatheter delivery system and a delivery system.

DESCRIPTION OF THE PRIOR ART

A diseased or defected heart valve can be repaired or replaced by implanting a prosthetic heart valve (hereinafter, prosthetic implant). The prosthetic implant is loaded at the distal end of the delivery system, and is delivered to the surgical site by intervention of the delivery system. If the prosthetic implant is improperly positioned within the native valve annulus during the expansion process, serious complications may occur.

The existing method is to recapture the prosthetic implant, that is, to recompress and reposition the completely or partially expanded prosthetic implant into the sheath of the delivery system. This process can also be called the retraction of the prosthetic implant. The term "retraction" and "recapture" here refer to the same meaning. After being retracted, the prosthetic implant is withdrawn outside the human body or repositioned in the human body.

The existing delivery system has the problem of stuck and unsmooth retracting, or the prosthetic implant damaging the sheath, resulting in failure of retraction.

SUMMARY OF THE DISCLOSURE

The present disclosure provides an expandable sheath for transcatheter delivery system to improve the smoothness of retracting the prosthetic implant.

The present disclosure provides an expandable sheath for transcatheter delivery system, which includes a tube having opposing distal and proximal ends in its axial direction. The distal end is provided with a plurality of support rods arranged at intervals in a circumferential direction of the tube, and the support rods extend axially and have relative converged and flared configurations. More than two connecting strips are provided in the axial direction between two adjacent support rods. The connecting strip has a curved extension path and undulates in the circumferential direction, and undulation degrees of the connecting strips increase sequentially from the proximal end to the distal end. The connecting strip has a first connecting portion and a second connecting portion respectively connected with two adjacent support rods in the circumferential direction, and the first connecting portion and the second connecting portion are located at different axial levels of the tube.

In the following, several alternatives are provided, but merely as further additions or preferences, instead of as additional limitations to the above-mentioned technical solution. Without technical or logical contradiction, the alternatives can be combined with the above-mentioned technical solution, individually or in combination.

Optionally, 3 to 4 connecting strips are arranged in the axial direction between two adjacent support rods.

Optionally, each connecting strip has more than two turning points.

Optionally, the connecting strip is substantially S-shaped with a peak and a valley.

Optionally, the peak of each connecting strip is located distally from the valley.

Optionally, the support rod is connected with an eyelet at a distal end thereof.

Optionally, a transition section is provided between the eyelet and the support rod, and the transition section has a smaller width than the support rod.

Optionally, the ratio of the width of the transition section to the width of the support rod is 1:2.0 to 3.0, for example, 1:2.5.

Optionally, one of the connecting portions of the most distal connecting strip is adjacent to the most distal end of the corresponding support rod.

Optionally, two axially adjacent connecting strips have connecting portions axially adjacent to each other and connected to different support rods.

Optionally, from the proximal end to the distal end, the lengths of the connecting strips along the respective extension paths increase sequentially or are equal to each other.

Optionally, axial spans of the connecting strips decrease sequentially from the proximal end to the distal end.

Optionally, from the proximal end to the distal end, the distances between two axially adjacent connecting ends on the same side of each support rod decreases gradually.

Optionally, from the proximal end to the distal end, a ratio of the axial span of one connecting strip to that of an adjacent connecting strip is 1.02 to 1.5:1, for example 1.05:1.

Optionally, a ratio of the axial span of the most proximal connecting strip to that of the most distal connecting strip is 1.05 to 2:1, for example 1.1:1.

Optionally, an area where the support rods are located is defined as an expansion section of the tube, and a section of the tube adjacent to a proximal end of the expansion section has a metal reinforcement layer, the metal reinforcement layer is a metal tube with a hollow structure, and the support rods, the connecting strips and the metal tube are formed in one piece.

Optionally, the tube further includes a middle section located at a proximal end of the expansion section, and the middle section is more readily flexible than the expansion section.

Optionally, both inner and outer sides of the metal reinforcement layer are provided with polymer covering film layers, and the inner and outer polymer covering film layers extend distally and past the expansion section and are connected with each other at the distal end to form a protective section.

The disclosure further provides a delivery system, including:
- a catheter assembly including the expandable sheath for transcatheter delivery system as described above and an inner shaft assembly,
- a prosthetic implant connected to a distal end of the inner shaft assembly; and
- a control handle, a proximal end of the catheter assembly is connected to the control handle.

When retracting the prosthetic implant, both sides of the support rod of the sheath according to the present disclosure are pulled by more than two curved connecting strips, until the support rod assumes a smooth arc shape, which makes the retracting of the prosthetic implant more smoothly. In the flared configuration, the expansion section with a strong structural strength and the flared opening prevent the prosthetic implant from being damaged, improving the success rate of the surgery.

Figure 1:
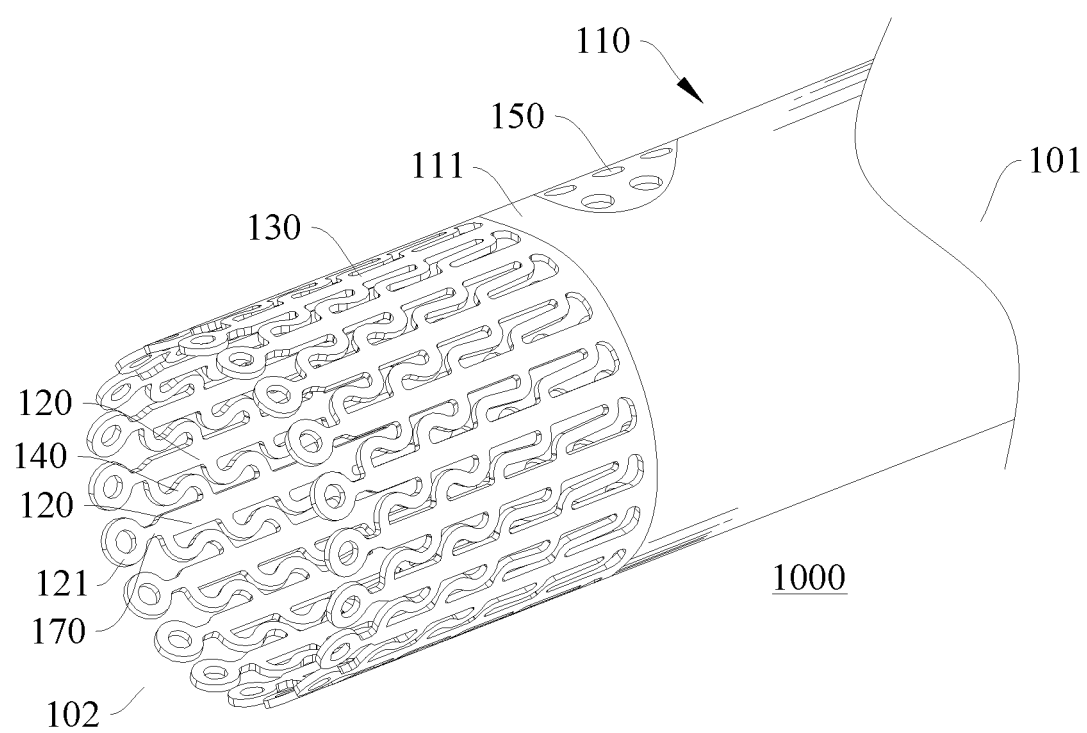
FIG. 1 is a schematic structural view of part of a sheath according to an embodiment of the present disclosure in a converged configuration (in order to show the structure of an expansion section more clearly, a polymer covering film layer is removed from the expansion section)

LIST OF REFERENCE SIGNS 1000, sheath; 110, tube; 101, proximal end; 102, distal end; 111, polymer covering film layer; 112, protective section;
120, support rod; 121, eyelet; 122, connecting portion;
130, expansion section;
140, connecting strip; 140a, first connecting strip; 140b, second connecting strip; 140c, third connecting strip; 140d, fourth connecting strip;
144, connecting end; 147, peak; 148, valley;
150, metal reinforcement layer; 161, first connecting portion; 162, second connecting portion; 170, transition section; 180, gap; 190, middle section;
2000, delivery system; 210, catheter assembly; 220, control handle; 230, inner shaft assembly;
3, prosthetic implant.

DESCRIPTION OF EMBODIMENTS

The technical solutions according to the embodiments of the present disclosure will be described clearly and fully in combination with the drawings according to the embodiments of the present disclosure. Obviously, the described embodiments are not all embodiments of the present disclosure, but only part of the embodiments of the present disclosure. Based on the disclosed embodiments, all other embodiments obtained by those skilled in the art without creative work fall into the scope of this invention.

It should be noted that, when a component is "connected" with another component, it may be directly connected to another component or may be indirectly connected to another component through a further component. When a component is "provided" on another component, it may be directly provided on another component or may be provided on another component through a further component.

Unless otherwise defined, all technical and scientific terms used herein have the same meaning as commonly understood by a person skilled in the art. The terms in the description of the present disclosure are used to describe specific embodiments, and not to limit the present disclosure. The term "and/or" used herein includes one or more of the listed options in any combinations, or the combination of all of the listed options.

In the present disclosure, the terms "first", "second" and the like are used for descriptive purposes only and are not to be understood as indicating or implying the relative importance or the number or order of the technical features referred. Thus, features defined with "first", "second" can explicitly or implicitly include one or more of such features. In the description of the present invention, "plurality" means at least two, such as two, three, etc., unless explicitly and specifically defined otherwise.

In the following drawings or descriptions, the prosthetic implant uses a prosthetic heart valve as an example. The prosthetic heart valve generally includes a deformable stent and leaflets connected within the stent. The stent is generally cylindrical, and the side wall thereof has a hollow meshed structure. Unless otherwise specified, the shape or size of the meshed structure is not strictly limited. The interior of the stent is a blood flow channel, and the leaflets cooperate with each other to open and control the blood flow channel within the stent. For positioning in the human body, the stent can be provided with positioning structures at the periphery, such as anchors, arms, and the like, that can engage with the surrounding native tissue.

The stent can be controlled by a wire, so that it can be retracted as desired during the release process. The stent can be formed by cutting a tube or braiding wires, and the leaflets can be connected to the stent by sewing, bonding or molding.

The stent generally has a connecting structure for engaging with the catheter assembly to limit each other, thereby preventing undesired deflection during delivery. The prosthetic implant has a radially compressed configuration during the interventional delivery, i.e., a loaded state, and a released state after being released from the catheter assembly and radially expanded in the human body.

For direction reference, the proximal end herein generally refers to the side adjacent to the operator (such as the physician), and the distal end refers to the side that is relatively far away from the operator. Each component has its own opposing distal and proximal ends in the intervention path. In theory, when the catheter assembly and the control handle are completely straightened, the straight line between the proximal end and the distal end defines the axis and thus the axial direction, and then the radial direction perpendicular to the axial direction and the circumferential direction around the axial direction can be determined. For structure reference, "end" herein refers to an end face of the structure or a certain point or a certain area at the corresponding side or a specific structure connected to the point or the area.

Figure 2:
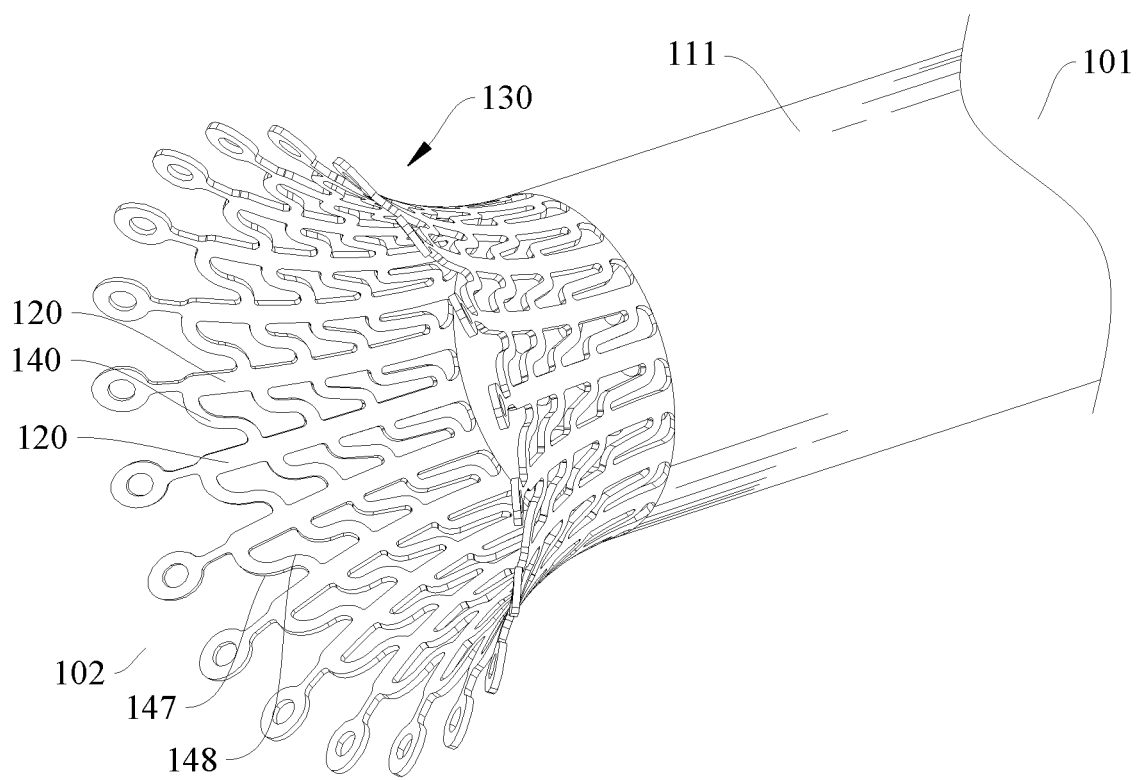
FIG. 2 is a schematic structural view of part of the sheath in FIG. 1 with the expansion section in a flared configuration.
Figure 3:
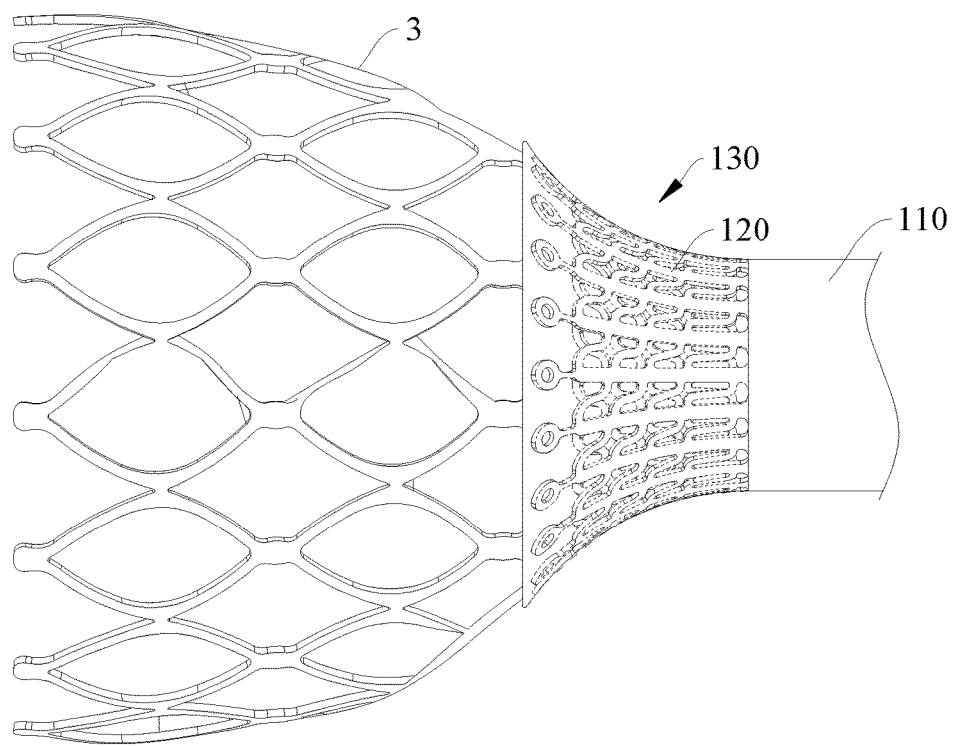
FIG. 3 is a schematic structural view of part of the sheath according to an embodiment of the present disclosure retracting a prosthetic implant.

As shown in FIGS. 1 to 5, the present disclosure provides an expandable sheath 1000 (hereinafter, sheath) for a transcatheter delivery system. The sheath includes a tube 110, and the tube 110 has opposing distal and proximal ends 102 and 101 in its axial direction. The distal end 102 includes a plurality of support rods 120 arranged at intervals in the circumferential direction of the tube. The support rods 120 have relatively converged and flared configurations, which two configurations mainly differ in the radial deformation of the support rods relative to the axis of the tube. In the axial direction of the tube, the support rods 120, as a whole, is configured as an expansion section 130, so that the expansion section 130 can also be considered having the configurations of the support rods 120. As shown in FIG. 1, the expansion section 130 has a straight cylindrical shape in the converged configuration. As shown in FIG. 2, in the flared configuration, the portions of the expansion section 130 in the axial direction are deformed away from the axis of the tube. When being retracted, the prosthetic implant 3 acts on the distal end of the sheath 1000, thereby driving the expansion section 130 to transform from the converged configuration to the flared configuration, as shown in FIG. 3. For the convenience of description, the length of the support rod 120 is defined in the axial direction of the tube, and the width is defined in the circumferential direction of the tube.

More than two connecting strips 140 are arranged between two adjacent support rods 120 in the axial direction of the tube. The connecting strips extend in curved paths and undulate in the circumferential direction. The undulation degrees of the connecting strips 140 increase in sequence from the proximal end to the distal end, wherein the undulation degree refers to the height in the circumferential direction at the highest undulating point. The connecting strip 140 has a first connecting portion 161 and a second connecting portion 162 respectively connected to two adjacent support rods 120 in the circumferential direction, and the first connecting portion 161 and the second connecting portion 162 are located at different axial levels of the tube.

Figure 4:
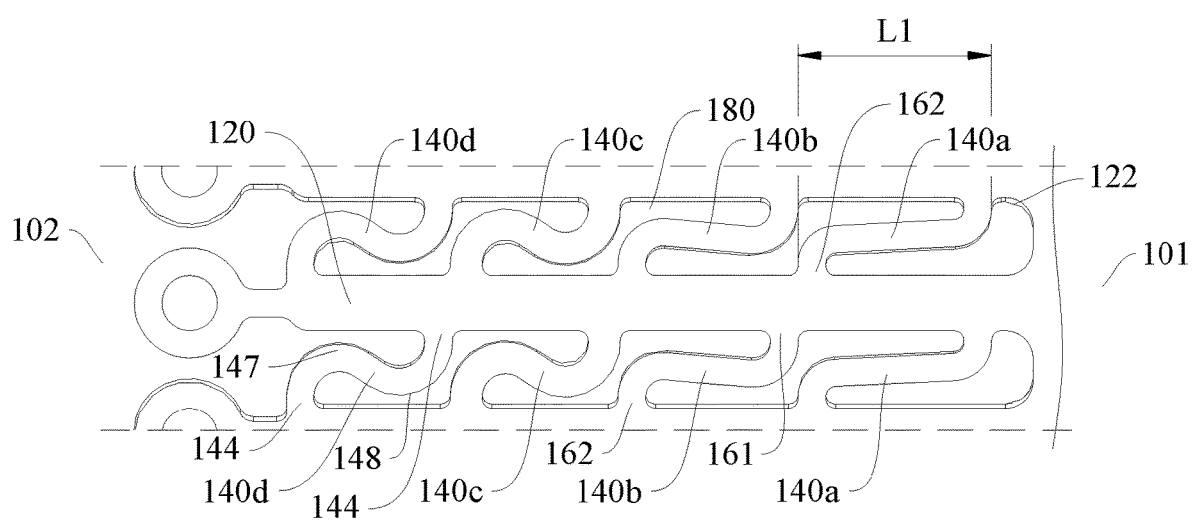
FIG. 4 is a schematic structural view of part of one support rod when the sheath according to an embodiment of the present disclosure is in the converged configuration.
Figure 5:
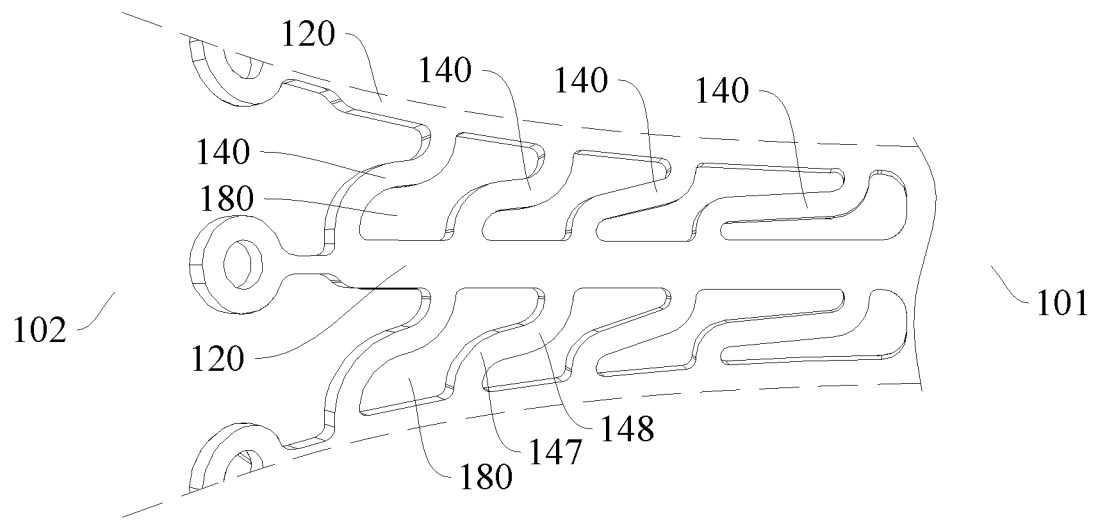
FIG. 5 is a schematic structural view of FIG. 4 when the sheath is in the flared configuration.

As shown in FIG. 4 and FIG. 5, the undulation degree of the connecting strip 140 affects its deformation during the flare process. The smaller the undulation degree, the straighter the connecting strip, the smaller the deformation, and the closer the connecting portion of the support rod connected with the connecting strip from the axis of the tube in the flared configuration; vice versa, the greater the undulation degree, the more twisted the connecting strip, the greater the deformation, and the farther the connecting portion of the support rod with the connecting strip from the axis of the tube in the flared configuration.

From the proximal end to the distal end, the undulation degrees of the connecting strips increase sequentially, so that the deformations of the portions of the support rod in its own axial direction increase gradually. In the flared configuration, the portions of the support rod 120 in its own axial direction, under the force from the connecting strips 140, finally maintain in a stable attitude to compress the prosthetic implant 3. In this attitude, the distance of the support rod 120 from the axis of the tube gradually increases from the proximal end to the distal end and thus the support rod 120 is arc-shaped. Correspondingly, the expansion section 130 is flared, which improves the smoothness of retracting the prosthetic implant. The turning portions of the connecting strips are arc-shaped, which reduces the stress concentration at the turning portions during the deformation, so that when the expansion section 130 is covered with a film (i.e., the polymer film layer below), the covering film would not be easily torn by the flared expansion section.

The connecting strip 140 undulates so that the gap 180 between adjacent support rods 120 can be defined more flexibly. For example, it can be ensured that the support rods themselves have a sufficient width and thus a strong structural strength, so that the expansion section 130 can form an ideal flared opening in the flared configuration; and an appropriate gap distance facilitates the arrangement of the connecting strips. In the flared configuration, the expansion section has a strong structural strength and a flared opening.

In one embodiment, 3 to 4 connecting strips 140 are arranged between two adjacent support rods 120 in the axial direction of the tube. The two ends of each connecting strip 140 are connecting ends 144, which are respectively located at the most distal and proximal ends of the connecting strip 140 in the axial direction. The connecting portion between the connecting end 144 and the support rod 120 is chamfered. The portion of the connecting strip 140 adjacent to its own connecting end is tangent to the support rod.

It should be noted that the connecting end of the connecting strip 140 is the same, in position, as the connecting portion where the connecting strip and the support rod are connected, and they are merely expressed differently in various contexts.

Figure 6:
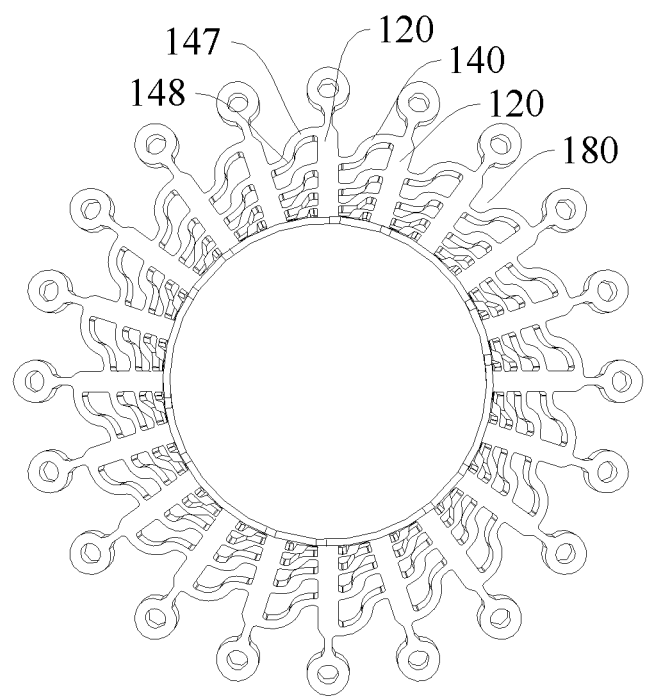
FIG. 6 is a left view of the sheath of FIG. 3 in the flared configuration.

In one embodiment, the same connecting strip 140 has more than two turning points (i.e., the above-mentioned turning portion). The turning point corresponds to the aforementioned highest undulating point. In a specific embodiment, the connecting strip 140 is generally S-shaped, with a peak 147 and a valley 148 corresponding to turning points. As shown in FIG. 5 and FIG. 6, the peak 147 and the valley 148 of the connecting strip are arranged facing towards the circumferential direction of the tube, and the peak 147 is located at the distal side of the valley 148. The peaks 147 of the connecting strips 140 face towards the same side in the circumferential direction of the tube, and the valleys 148 face towards the other side in the circumferential direction of the tube. The deformation directions of the peaks and valleys during the flare process are generally the same, which prevents the covering film (i.e., the polymer covering film layer below) from being torn during the flare process due to different deformation trends of the connecting strips.

If the peak 147 of the connecting strip is arranged towards the axial direction, within the limited gap 180, the width of the connecting strip itself (relative to the extending direction of the connecting strip itself) will need to be reduced to meet the twist requirement, resulting in uncontrollable deformation. Therefore, the peak 147 arranged towards the circumferential direction helps to ensure that the connecting strip has a sufficient width within the limited gap 180 to maintain an appropriate attitude in the flared configuration.

In some embodiments, the connecting ends on two sides of the support rod 120 are aligned to or offset from each other in the axial direction. Two axially adjacent connecting strips, for example, each has a connecting portion that is axially adjacent to each other and connected to different support rods. As shown in FIG. 4, for example, the two connecting ends of each connecting strip 140 are respectively the first connecting end (that is, the first connecting portion 161) and the second connecting end (the second connecting portion 162) from the proximal end to the distal end. The connecting strips 140 include a first connecting strip 140a, a second connecting strip 140b, a third connecting strip 140c and a fourth connecting strip 140d from the proximal end to the distal end.

For each support rod 120, the second connecting portion 162 of the first connecting strip 140a on one side and the first connecting portion 161 of the second connecting strip 140b on the other side are adjacent to each other. Such arrangement increases the acting points of the same number of connecting strips on the support rod 120 in the axial direction, and two adjacent acting points avoid circumferential twisting of the support rod 120 during the flare process.

Within two adjacent connecting strips, the proximal surface of the distal connecting strip and the distal surface of the proximal connecting strip are at the same axial level or extend over each other. For example, the distal surface of the first connecting strip 140a is substantially at the same axial level as the proximal surface of the second connecting strip 140b; the distal surface of the second connecting strip 140b extends over the proximal surface of the third connecting strip 140c; the distal surface of the third connecting strip 140c extends over the proximal surface of the fourth connecting strip 140d. In other words, adjacent connecting strips coincide with each other in the axial direction, permitting the efficient use of space.

In some embodiments, the distal end of the support rod 120 is further connected with an eyelet 121. The eyelet 121 can reduce safety risk and a contrast element can be further provided therein. In one embodiment, the tube 110 includes a transition section 170 connected to the distal end of the support rod 120. The transition section 170 has the same extension tendency as the support rod 120 in the converged configuration. The transition section 170 and the support rod 120 extend with equal width, respectively, and the width of the transition section 170 is smaller than the width of the support rod 120. Specifically, the width ratio of the transition section 170 to the support rod 120 is 1:2.0 to 3.0, preferably 2.5. The ratio of the outer diameter of the eyelet 121 to the width of the support rod 120 is 1.5 to 3:1, preferably 2:1.

In one embodiment, one connecting portion of the most distal connecting strip 140 is adjacent to the most distal end (i.e., the connecting portion between the support rod 120 and the transition section 170) of the corresponding support rod 120, enhancing the structural strength of the support rod 120 at the distal end thereof. The most distal connecting portion of the connecting strip 140 located at the most distal end of the support rod 120 increases the contact area of the distal end of the expansion section 130 with the prosthetic implant, which facilitates the retraction.

In one embodiment, the lengths (extension lengths) of the connecting strips 140 increase sequentially from the proximal end to the distal end. The length variation of the connecting strips 140 adapts to the deformation of the support rods 120 at different positions in the axial direction. The length variation of the connecting strips 140 and the twist variation of the connecting strips 140 cooperate to adapt to the deformation of the support rods, so that enough connecting strips 140 can be arranged in a limited space.

In another embodiment, from the proximal end to the distal end, the lengths (extension lengths) of the connecting strips 140 are equal to each other. It is the twist of the connecting strips 140 that mainly adapt to the deformation of the support rods.

In another embodiment, from the proximal end to the distal end, the lengths (extension lengths) of the connecting strips 140 decrease sequentially.

In one embodiment, from the proximal end to the distal end, the axial spans L1 of the connecting strips 140 decrease sequentially. From the proximal end to the distal end, the distances between each two axially adjacent connecting ends 144 on the same side of the corresponding support rod 120 decrease gradually in the extending direction of the support rod 120.

From the proximal end to the distal end, the ratio of the axial span of one connecting strip to that of an adjacent connecting strip is 1.02 to 1.5:1; for example 1.05:1; the ratio of the axial span of the most proximal connecting strip to that of the most distal connecting strip is 1.05 to 2:1; for example, 1.1:1.

In another embodiment, from the proximal end to the distal end, the axial spans L1 of the connecting strips 140 are the same.

In one embodiment, the section of the tube 110 adjacent to a proximal end of the expansion section has a metal reinforcement layer 150. The metal reinforcement layer 150 is a metal tube with a hollow structure, which is formed in one piece with the support rods 120 and the connecting strips 140, for example, by cutting a tube. As shown in FIG. 4, the support rods 120 are connected with the metal tube, and the connecting portions 122 of the two are chamfered. When retracting the prosthetic implant, the section with the metal reinforcement layer is not flared.

The metal tube is connected with the expansion section 130 and the length of the metal tube is not strictly limited. For example, the axially proximal end of the metal tube can be located proximally from the proximal end of the prosthetic implant that is compressed in the tube.

Figure 7:
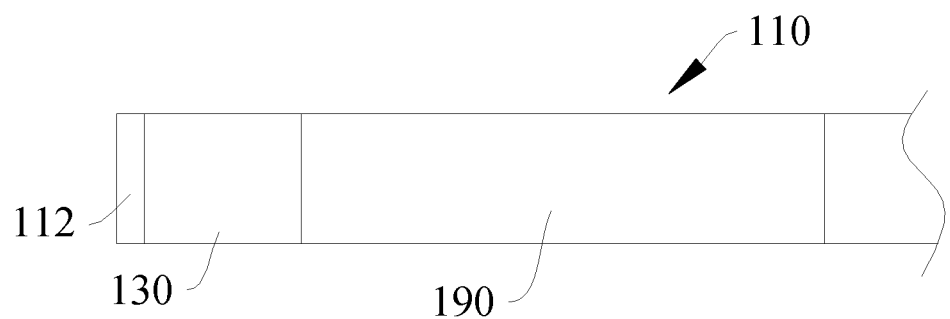
FIG. 7 is a schematic structural view of a distal end of the sheath according to an embodiment of the present disclosure.
Figure 8:
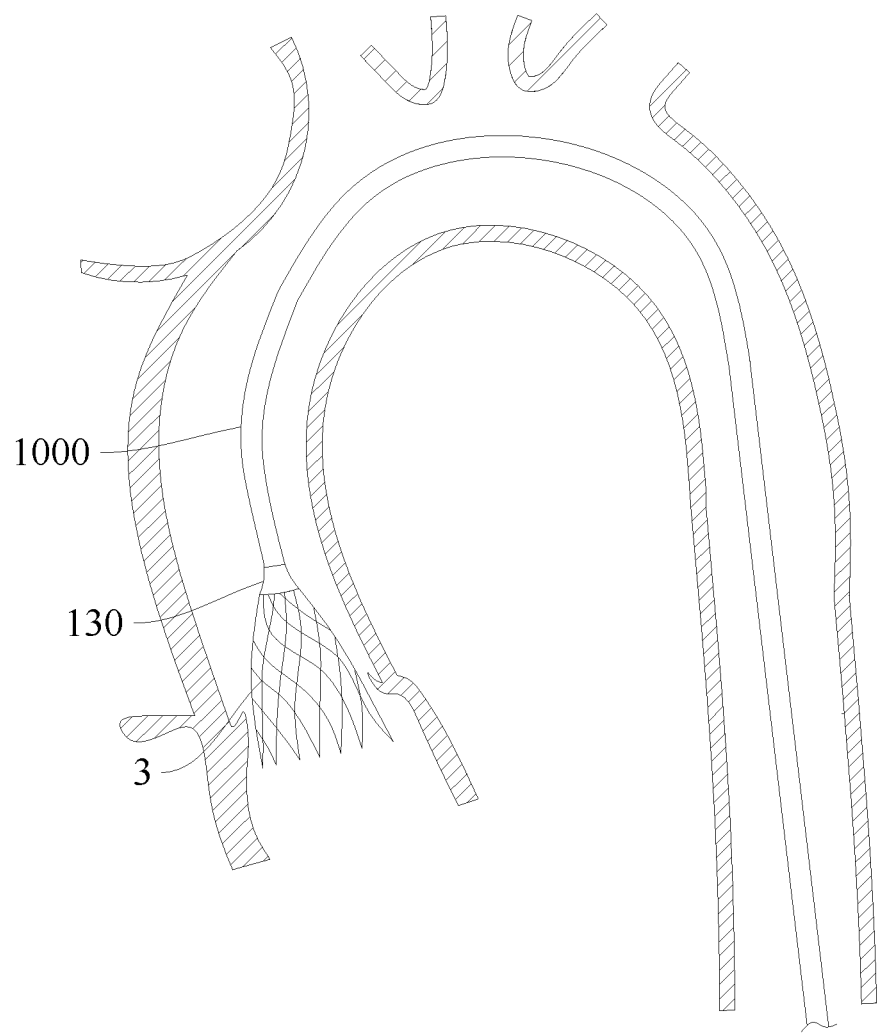
FIG. 8 is a schematic structural view of the sheath according to an embodiment of the present disclosure retracting a prosthetic implant in the human body.

As shown in FIG. 7 and FIG. 8, in one embodiment, the tube 110 further includes a middle section 190 located at the proximal end of the expansion section. The middle section 190 is more readily flexible than the expansion section 130, which facilitates passing through the curved portion in the human body, such as the aortic arch.

Both inner and outer sides of the metal reinforcement layer 150 are provided with polymer covering film layers 111. The polymer covering film layer 111 is made of a transparent or opaque material. For convenience of observation, the polymer covering film layer in FIG. 1 and FIG. 2 is shown in an opaque form. As shown in FIG. 7, the polymer covering film layer 111 extends to the distal end to cover the expansion section 130, and the inner and outer polymer covering film layers 111 meet and connect with each other, for example, by fuse, at the distal end to form a protective section 112, which improves the connection strength of the inner and the outer polymer covering film layers 111 and covers the expansion section more broadly, reducing the risk of tissue damage during the intervention of the sheath.

Figure 9:
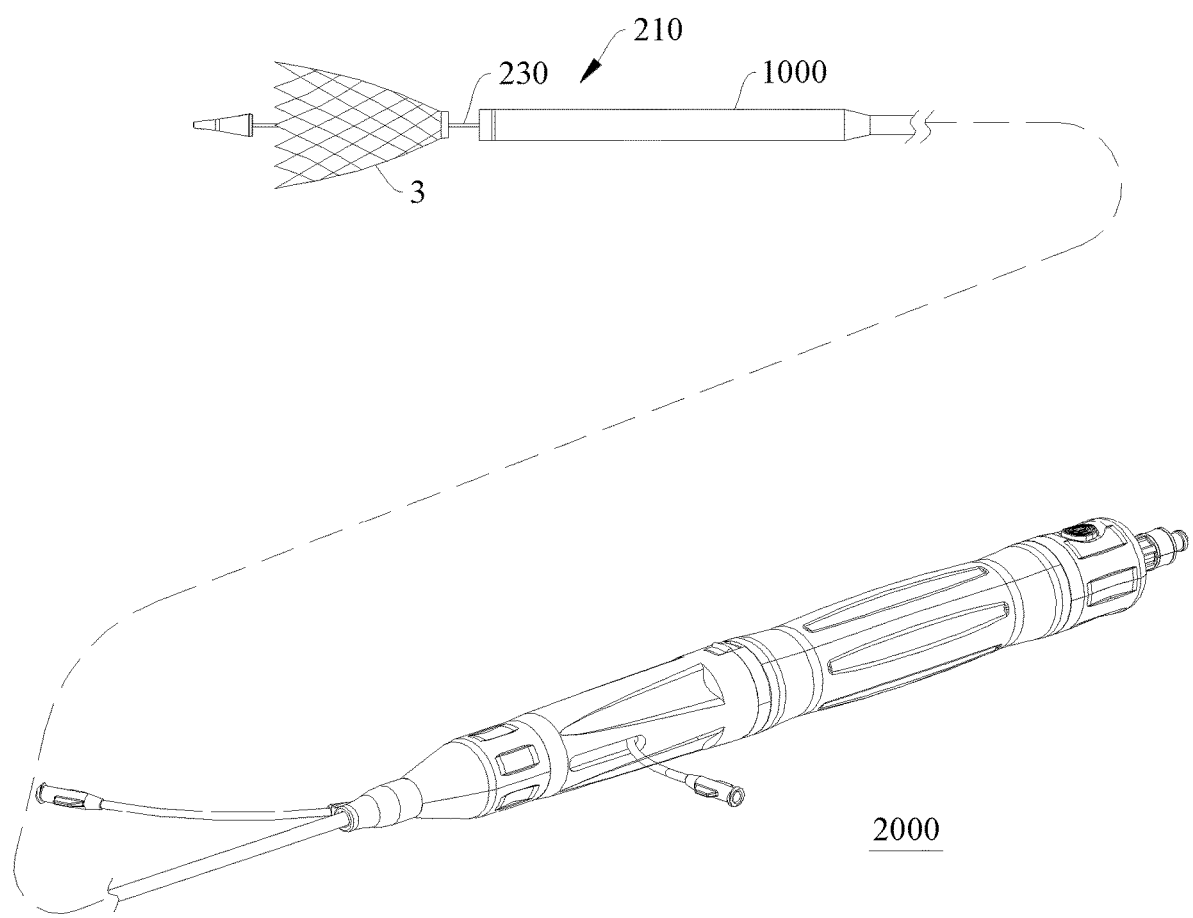
FIG. 9 is a schematic structural diagram of a delivery system according to an embodiment of the present disclosure.

As shown in FIGS. 8 and 9, the present disclosure further provides a delivery system 2000, including a catheter assembly 210 and a control handle 220. The catheter assembly 210 includes the sheath 1000 according to the above-mentioned embodiments and an inner shaft assembly 230. The prosthetic implant is connected to the distal end of the inner shaft assembly 230. The sheath 1000 has an initial state of covering the prosthetic implant, and a release state in which it is moved relative to the inner shaft assembly 230 so as to completely expose the prosthetic implant. The proximal end of the catheter assembly 210 is connected to the control handle 220 in a controllable manner. The specific structure of the catheter assembly and the control handle can use the existing techniques.

The retraction process is described in detail below:

The control handle 220 drives the sheath 1000 to move distally, so that the sheath 1000 moves axially relative to the inner shaft assembly 230, and the expansion section of the sheath acts on the prosthetic implant 3 until the prosthetic implant is completely retracted into the sheath.

When retracting the prosthetic implant, both sides of the support rod of the sheath according to the present disclosure are pulled by more than two curved connecting strips, until the support rod assumes a smooth arc shape, which makes the retracting of the prosthetic implant more smoothly. In the flared configuration, the expansion section with a strong structural strength and the flared opening prevent the prosthetic implant from being damaged, improving the success rate of the surgery.

The technical features of the above embodiments can be arbitrarily combined, and not all possible combinations of the technical features of the above embodiments have been described for the sake of brevity of description. However, as long as there is no contradiction in the combination of these technical characteristics, such combination should be regarded as falling into the scope of this specification. When the technical features in different embodiments are shown in the same drawing, it can be considered that the drawing also discloses a combined embodiment of various embodiments involved.

The above-described embodiments only illustrate several embodiments of the present disclosure, and the description thereof is specific and detail, but should not be construed as limiting the scope of the patent disclosure. It should be noted that, for those of ordinary skill in the art, several modifications and improvements can be made without departing from the concept of the present disclosure, all of which fall into the protection scope of the present disclosure.

The invention claimed is:

1. An expandable sheath for transcatheter delivery system, comprising a tube having opposing distal and proximal ends in its axial direction, the distal end being provided with a plurality of support rods arranged at intervals in a circumferential direction of the tube, and the support rods extending axially and having relative converged and flared configurations, wherein more than two connecting strips are provided in the axial direction between two adjacent support rods, each of the connecting strips has a curved extension path and undulates in the circumferential direction, and undulation degrees of the connecting strips increase sequentially from a proximal end to a distal end of the plurality of support rods, and wherein each of the connecting strips has a first connecting portion and a second connecting portion respectively connected with two adjacent support rods in the circumferential direction, and the first connecting portion and the second connecting portion are located at different axial levels of the tube.

2. The expandable sheath for transcatheter delivery system according to claim 1, wherein 3 to 4 connecting strips are arranged in the axial direction between two adjacent support rods.

3. The expandable sheath for transcatheter delivery system according to claim 1, wherein each connecting strip has more than two turning points.

4. The expandable sheath for transcatheter delivery system according to claim 1, wherein each connecting strip is substantially S-shaped with a peak and a valley.

5. The expandable sheath for transcatheter delivery system according to claim 1, wherein the plurality of support rods are each connected with an eyelet at a distal end thereof.

6. The expandable sheath for transcatheter delivery system according to claim 5, wherein a transition section is provided between each of the support rods and a corresponding eyelet, and the transition section has a smaller width than a corresponding support rod.

7. The expandable sheath for transcatheter delivery system according to claim 1, wherein the connecting strips comprise a most distal connecting strip, and one of the first and second connecting portions of the most distal connecting strip is adjacent to a distal end of a corresponding support rod.

8. The expandable sheath for transcatheter delivery system according to claim 1, wherein two axially adjacent connecting strips have the first and second connecting portions axially adjacent to each other and connected to different support rods.

9. The expandable sheath for transcatheter delivery system according to claim 1, wherein from the proximal end to the distal end of the plurality of support rods, lengths of the connecting strips along the respective extension paths increase sequentially or are equal to each other.

10. The expandable sheath for transcatheter delivery system according to claim 1, wherein axial spans of the connecting strips decrease sequentially from the proximal end to the distal end of the plurality of support rods.

11. The expandable sheath for transcatheter delivery system according to claim 10, wherein from the proximal end to the distal end of the plurality of support rods, a ratio of an axial span of one connecting strip to that of an adjacent connecting strip is 1.02 to 1.5:1.

12. The expandable sheath for transcatheter delivery system according to claim 10, wherein the connecting strips comprise a most proximal connecting strip and a most distal connecting strip, and a ratio of an axial span of the most proximal connecting strip to that of the most distal connecting strip is 1.05 to 2:1.

13. The expandable sheath for transcatheter delivery system according to claim 1, wherein an area where the support rods are located is defined as an expansion section of the tube, and a section of the tube adjacent to a proximal end of the expansion section has a metal reinforcement layer, the metal reinforcement layer is a metal tube with a hollow structure, and the support rods, the connecting strips and the metal tube are formed in one piece.

14. The expandable sheath for transcatheter delivery system according to claim 13, wherein the tube further comprises a middle section located at the proximal end of the expansion section, and the middle section is more readily flexible than the expansion section.

15. The expandable sheath for transcatheter delivery system according to claim 13, wherein inner and outer sides of the metal reinforcement layer are respectively provided with inner and outer polymer covering film layers, and the inner and outer polymer covering film layers extend distally and past the expansion section and are connected with each other at the distal end of the tube to form a protective section.

16. A delivery system, comprising:
a catheter assembly comprising the expandable sheath for transcatheter delivery system according to claim 1 and an inner shaft assembly,
a prosthetic implant connected to a distal end of the inner shaft assembly; and
a control handle, a proximal end of the catheter assembly is connected to the control handle.

* * * * *